United States Patent
Højlund Nielsen et al.

(10) Patent No.: US 11,331,638 B2
(45) Date of Patent: *May 17, 2022

(54) INDUCTION HEATED AROMATIZATION OF HIGHER HYDROCARBONS

(71) Applicant: HALDOR TOPSØE A/S, Kgs. Lyngby (DK)

(72) Inventors: Poul Erik Højlund Nielsen, Fredensborg (DK); Peter Mølgaard Mortensen, Roskilde (DK); Kim Aasberg-Petersen, Allerød (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 464 days.

This patent is subject to a terminal disclaimer.

(21) Appl. No.: 16/086,037

(22) PCT Filed: Mar. 31, 2017

(86) PCT No.: PCT/EP2017/057670
§ 371 (c)(1),
(2) Date: Sep. 18, 2018

(87) PCT Pub. No.: WO2017/186452
PCT Pub. Date: Nov. 2, 2017

(65) Prior Publication Data
US 2020/0290003 A1    Sep. 17, 2020

(30) Foreign Application Priority Data
Apr. 26, 2016    (DK) .......................... PA 2016 00245

(51) Int. Cl.
*B01J 8/00* (2006.01)
*B01J 8/02* (2006.01)
(Continued)

(52) U.S. Cl.
CPC .............. *B01J 8/0285* (2013.01); *B01J 8/025* (2013.01); *B01J 8/0278* (2013.01); *B01J 23/862* (2013.01);
(Continued)

(58) Field of Classification Search
CPC ..... B01J 8/00; B01J 8/02; B01J 8/0242; B01J 8/025; B01J 8/0278; B01J 8/0285;
(Continued)

(56) References Cited

U.S. PATENT DOCUMENTS

| 4,229,234 A | 10/1980 | Krutenat et al. |
| 5,609,751 A | 3/1997 | Wall |

(Continued)

FOREIGN PATENT DOCUMENTS

| FR | 3 003 774 A1 | 10/2014 |
| GB | 2 210 286 A | 6/1989 |

(Continued)

OTHER PUBLICATIONS

Danish Search Report of Danish Patent Application No. PA 2016 00245, dated Nov. 15, 2016.
(Continued)

*Primary Examiner* — Natasha E Young
(74) *Attorney, Agent, or Firm* — Buchanan Ingersoll & Rooney P.C.

(57) ABSTRACT

A reactor system for aromatization of higher hydrocarbons within a given temperature range T upon bringing a reactant stream including higher hydrocarbons into contact with a catalytic mixture. The reactor system includes a reactor unit arranged to accommodate a catalytic mixture. The catalytic mixture includes a catalyst material and a ferromagnetic material. The catalyst material is arranged to catalyze the aromatization of higher hydrocarbons. The ferromagnetic material is ferromagnetic at least at temperatures up to an
(Continued)

upper limit of the given temperature range T, where the temperature range T is the range from between about 400° C. and about 700° C. or a subrange thereof. The reactor system also includes an induction coil arranged to be powered by a power source supplying alternating current, whereby the ferromagnetic material is heated to a temperature within the temperature range T by means of an alternating magnetic field.

14 Claims, 2 Drawing Sheets

(51) Int. Cl.
| | |
|---|---|
| *B01J 23/86* | (2006.01) |
| *B01J 29/04* | (2006.01) |
| *B01J 29/85* | (2006.01) |
| *B01J 35/00* | (2006.01) |
| *C07C 2/42* | (2006.01) |
| *B01J 29/06* | (2006.01) |

(52) U.S. Cl.
CPC .............. *B01J 29/061* (2013.01); *B01J 29/85* (2013.01); *B01J 35/0033* (2013.01); *C07C 2/42* (2013.01); *B01J 2208/00433* (2013.01); *C07C 2523/06* (2013.01); *C07C 2529/06* (2013.01); *C07C 2529/85* (2013.01)

(58) Field of Classification Search
CPC ... B01J 23/00; B01J 23/70; B01J 23/76; B01J 23/84; B01J 23/85; B01J 23/86; B01J 23/862; B01J 29/00; B01J 29/04; B01J 29/06; B01J 29/061; B01J 29/82; B01J 29/84; B01J 29/85; B01J 35/00; B01J 35/002; B01J 35/0033; B01J 2208/00; B01J 2208/00008; B01J 2208/00017; B01J 2208/00433; C07C 2/00; C07C 2/02; C07C 2/42; C07C 2523/00; C07C 2523/06; C07C 2529/00; C07C 2529/04; C07C 2529/06; C07C 2529/82; C07C 2529/84; C07C 2529/85

See application file for complete search history.

(56) References Cited

U.S. PATENT DOCUMENTS

| | | | |
|---|---|---|---|
| 5,958,273 | A | 9/1999 | Koch et al. |
| 6,315,972 | B1 | 11/2001 | Mehdizadeh et al. |
| 7,365,289 | B2 * | 4/2008 | Wilkes ................... B01J 8/0015 |
| | | | 219/634 |
| 9,713,809 | B2 * | 7/2017 | Chaudret .............. B01J 35/0013 |
| 10,987,646 | B2 * | 4/2021 | Hojlund Nielsen ... B01J 35/026 |
| 2003/0175196 | A1 | 9/2003 | Blackwell et al. |
| 2010/0048969 | A1 | 2/2010 | Lauritzen et al. |
| 2010/0249404 | A1 | 9/2010 | Friese et al. |
| 2016/0023201 | A1 | 1/2016 | Chaudret et al. |
| 2018/0243711 | A1 * | 8/2018 | Mortensen ............... B01J 23/78 |

FOREIGN PATENT DOCUMENTS

| | | | | |
|---|---|---|---|---|
| JP | 2004-250255 | A | 9/2004 | |
| WO | 95/21126 | A1 | 8/1995 | |
| WO | WO-2013163118 | A1 * | 10/2013 | ............... C07C 2/76 |
| WO | WO-2014162099 | A1 * | 10/2014 | ............. C10G 2/332 |

OTHER PUBLICATIONS

International Search Report (PCT/ISA/210) dated Jun. 9, 2017, by the European Patent Office as the International Searching Authority for International Application No. PCT/EP2017/057670.
Written Opinion (PCT/ISA/237) dated Jun. 9, 2017, by the European Patent Office as the International Searching Authority for International Application No. PCT/EP2017/057670.

\* cited by examiner

INDUCTION HEATED AROMATIZATION OF HIGHER HYDROCARBONS

This application is a national stage application of International Application No. PCT/EP2017/057670, filed on Mar. 31, 2017, which claims priority to Danish Patent Application No. PA 2016 00245, filed on Apr. 26, 2016.

The present invention relates to a reactor system for aromatization of higher hydrocarbons, to a catalytic mixture arranged for catalyzing aromatization of higher hydrocarbons in a reactor, and to a method for aromatization of higher hydrocarbons.

Aromatic compounds, such as benzene, toluene and xylene, can be produced from higher hydrocarbons, such as propane, butane and pentane. Current state of the art in industrial processes for aromatization of higher hydrocarbons typically comprises an initial dehydrogenation of alkanes followed by aromatization of the alkenes.

The reaction is thermodynamically controlled and takes place at temperatures of about 500-700° C., typically without any co-feed or diluents. Typically, a feed or a reactant stream comprising higher hydrocarbons is preheated in a separate preheat section prior to entering the reactor(s) in which the dehydrogenation and aromatization takes place, and typically the reaction occurs adiabatically in sequential reactors, possibly with heating in between.

The initial dehydrogenation is endothermic, whilst the subsequent aromatization is exothermic. Overall, the reaction enthalpy ends up being almost thermo neutral.

One of the parasitic reactions in dehydrogenation is carbon formation, which leads to rapid deactivation of the catalyst. Thus, frequent regenerations of the catalyst may be necessary in certain applications. Carbon formation is not only a problem for the catalyst. Also the material used for the dehydrogenation reactor and for the piping has to be carefully selected, typically by using highly expensive alloys in order to avoid carbon attack resulting in the catastrophic form of corrosion known as metal dusting.

The combination of high temperatures and a dry hydrocarbon feed in the dehydrogenation and aromatization reaction results in a high potential for carbon formation in the catalyst bed and the preheat section.

It is therefore an object of the present invention to provide a process, reactor system and catalyst mixture for aromatization of alkanes which are able to maintain a high stability of the catalyst and reactor system.

It is another object of the present invention to provide a process, reactor system and catalyst mixture for aromatization of alkanes which are simple and energy efficient and which at the same time enables maintaining high stability of the catalyst.

It is also an object of the present invention to provide a process, reactor system and catalyst mixture wherein the reaction temperature is controlled accurately. Preferably, the temperature of the process is lowered compared to hitherto known reactions; hereby, the thermodynamic potential for dehydrogenation is increased and parasitic reactions, such as coking and/or cracking of the catalyst material are reduced.

The present invention solves one or more of the above mentioned problems.

An aspect of the present invention relates to a reactor system for aromatization of higher hydrocarbons within a given temperature range T upon bringing a reactant stream comprising higher hydrocarbons into contact with a catalytic mixture. The reactor system comprises a reactor unit arranged to accommodate a catalytic mixture, said catalytic mixture comprising a catalyst material and a ferromagnetic material, where the catalyst material is arranged to catalyze the aromatization of higher hydrocarbons and said ferromagnetic material is ferromagnetic at least at temperatures up to an upper limit of the given temperature range T, where the temperature range T is the range from between about 400° C. and about 700° C. or a subrange thereof. The reactor system also comprises an induction coil arranged to be powered by a power source supplying alternating current and being positioned so as to generate an alternating magnetic field within the reactor unit upon energization by the power source, whereby the ferromagnetic material is heated to a temperature within said temperature range T by means of said alternating magnetic field.

A key element, which the present invention addresses, is the issue of supplying heat needed to carry out the dehydrogenation reaction. The reaction is often carried out in more than one adiabatic catalytic bed, with reheating in between or in a reactor with a furnace, e.g. an electric furnace. By the reactor system of the invention, the heat for the endothermic dehydrogenation reaction is provided by induction heating. This provides for a quick heating of the catalyst within the reactor. Moreover, a good control of the temperature within the reactor system is obtained, which in turn assists in reducing carbon formation on the catalyst and in maximizing the conversion of alkanes to alkenes.

In general, the temperature within the reactor unit may be kept lower than would be the case with an externally heated reactor or with a preheated stream. This provides for an improved overall yield, a better selectivity as well as a quicker start-up of the process. Moreover, less catalyst degeneration in the form of coking and cracking will happen, thus reducing the frequency of regenerations of the catalyst.

In the reactor system of the invention, the catalytic mixture, viz. the ferromagnetic material, will be the hottest part of the system. The temperature difference across the bed will however be dependent on the actual configuration of the ferromagnetic material, the catalyst material and the process conditions.

Preferably, the coercivity of the ferromagnetic material is high, so that the amount of heat generated within the ferromagnetic material and dissipated by the external field in reversing the magnetization in each magnetization cycle is high.

As used herein, a material of "high magnetic coercivity", $_BH_C$, is seen as a "hard magnetic material" having a coercivity $_BH_C$ at or above about 20 kA/m, whilst a material of "low magnetic coercivity" is seen as a "soft magnetic material" having a coercivity $_BH_C$ at or below about 5 kA/m. It should be understood that the terms "hard" and "soft" magnetic materials are meant to refer to the magnetic properties of the materials, not their mechanical properties.

As used herein, the term "temperature range T" is meant to denote a desired range of temperatures, typically up to an upper limit thereof, at which the dehydrogenation reaction is to take place within the reactor system during operation. The temperature range T is the range from between about 400° C. and about 700° C. or a subrange thereof. Preferred subranges are e.g. the range from between about 450° C. and about 700° C., the range from between about 500° C. and about 700° C., the range from between about 550° C. and about 700° C., or the range from between about 550° C. and about 650° C.

As used herein, the term "higher hydrocarbons" is meant to denote organic compound consisting entirely of hydrogen and carbon and including at least three carbon molecules.

Ferromagnetic material provides for further advantages, such as:

A ferromagnetic material absorbs a high proportion of the magnetic field, thereby making the need for shielding less or even superfluous.

Heating of ferromagnetic materials is relatively faster and cheaper than heating of non-ferromagnetic materials. A ferromagnetic material has an inherent or intrinsic maximum temperature of heating, viz. the Curie temperature. Therefore, the use of a catalyst material which is ferromagnetic ensures that an endothermic chemical reaction is not heated above a specific temperature, viz. the Curie temperature. Thus, it is ensured that the chemical reaction will not run out of control.

Another advantage of the invention is that the temperature of the reactor unit can be kept lower than the temperature of the conventionally used adiabatic reactor. The lower temperature is beneficial for the overall yield of the process and required regenerations for carbon removal will be less frequent since parasitic reactions like coking and cracking are reduced. Further advantages comprise the possibility of tuning the exit temperature, which increases the thermodynamic potential for dehydrogenation.

The induction coil may e.g. be placed within the reactor unit or around the reactor unit. If the induction coil is placed within the reactor unit, it is preferable that it is positioned at least substantially adjacent to the inner wall(s) of the reactor unit in order to surround as much of the catalytic mixture as possible. In the cases, where the induction coil is placed within the reactor unit, windings of the reactor unit may be in physical contact with catalyst material. In this case, in addition to the induction heating, the catalyst material may be heated directly by ohmic/resistive heating due to the passage of electric current through the windings of the induction coil. The reactor unit is typically made of non-ferromagnetic material.

In conclusion, the invention provides a reactor system arranged to carry out aromatization of higher hydrocarbons cheaper and with better selectivity than current reactor systems. Moreover, the lifetime of the catalyst will be improved due to the lower average operation temperature within the reactor system.

In an embodiment, the Curie temperature of the ferromagnetic material equals an operating temperature at substantially the upper limit of the given temperature range T of the aromatization reaction. The term "aromatization reaction" is meant to denote the full reaction from dehydrogenation of alkanes to alkenes and the subsequent aromatization of alkenes to aromatic compound, unless it is specified that the term only denotes the subsequent aromatization of alkenes to aromatic compounds.

The Curie temperature of the ferromagnetic material could be close to, above or far above the upper limit of the given temperature range T. In an embodiment the Curie temperature equals an operating temperature at substantially the upper limit of the given temperature range T, thereby providing an upper limit of the temperature range T Hereby, it is ensured that the dehydrogenation reaction is not heated above a specific temperature, viz. the Curie temperature. Thus, it is ensured that the temperature does not become too high; it is well known that excessive temperatures may give rise to significant coke formation due to thermal cracking. Thus, designing the composition of the catalyst in order to design the Curie temperature renders it possible to provide a catalyst that will be less prone to carbon formation.

In an embodiment, the Curie temperature of the ferromagnetic material is above about 500° C. Typically the Curie temperature of the ferromagnetic material is below about 1000° C. As an example only, the ferromagnetic material is FeCrAlloy with a Curie temperature of about 560° C.

In an embodiment, the induction coil is placed within the reactor unit or around the reactor unit. The coil may e.g. be made of copper, constantan, an iron-chromium-aluminium (FeCrAl) alloy, an alloy of copper, manganese, and nickel, and combinations thereof. An iron-chromium-aluminum alloy is e.g. sold under the trademark "Kanthal", and an alloy of copper, manganese and nickel is sold under the trademark "Manganin". The examples of the material of the induction coil are advantageous due to their low resistivity and high temperature stability. Other materials which fulfil these requirements could also be considered for the application.

In an embodiment, the ferromagnetic material comprises one or more ferromagnetic macroscopic supports susceptible for induction heating, where the one or more ferromagnetic macroscopic supports are ferromagnetic at temperatures up to an upper limit of the given temperature range T, where the one or more ferromagnetic macroscopic supports is/are coated with an oxide and where the oxide is impregnated with catalyst material. The ferromagnetic material may e.g. be cobalt, iron, nickel, an alnico alloy, a FeCr alloy, Permendur or combinations thereof.

The oxide may also be impregnated with ferromagnetic particles. Thus, when the catalyst material is subjected to a varying magnetic field, both the ferromagnetic macroscopic support and the ferromagnetic particles impregnated into the oxide of the ferromagnetic macroscopic support are heated. Whilst the ferromagnetic macroscopic support heats the catalyst material from within, the ferromagnetic particles heats from the outside of the oxide. Thereby, a higher temperature and/or a higher heating rate are/is achievable.

As used herein, the term "macroscopic support" is meant to denote a macroscopic support material in any appropriate form providing a high surface. Non-limiting examples are metallic elements, monoliths or miniliths. The macroscopic support may have a number of channels; in this case it may be straight-channeled or a cross-corrugated element. The material of the macroscopic support may be porous or the macroscopic support may be a solid. The word "macroscopic" in "macroscopic support" is meant to specify that the support is large enough to be visible with the naked eye, without magnifying devices.

In an embodiment, the catalytic mixture comprises bodies of catalyst material mixed with bodies of ferromagnetic material, wherein the smallest outer dimension of a plurality of the bodies are in the order of about 1-2 mm or larger. Preferably, the smallest outside dimension of the bodies are between about 2-3 mm to about 8 mm. The bodies of catalyst material are e.g. extrudates or miniliths. The bodies of ferromagnetic material may e.g. be iron spheres. The term "miniliths" is meant to denote a small monolith; a reactor may typically house a large number of miniliths.

The catalytic mixture preferably has a predetermined ratio between said bodies of catalyst material and said bodies of ferromagnetic material. The predetermined ratio between said catalyst and said ferromagnetic materials is preferably a predetermined graded ratio varying along a flow direction of said reactor. Hereby, it is possible to control the temperature in different zones of the reactor. A radial flow reactor may be used; in this case, the predetermined ration varies along the radial direction of the reactor. Alternatively, an axial flow reactor may be used. The ferromagnetic material may e.g. be cobalt, iron, nickel, an alnico alloy, a FeCr alloy, Permendur or combinations thereof.

In an embodiment, the distance between windings of said induction coil varies along the flow direction of the reactor. Hereby, the heating within the reactor may be graded by varying the distance between windings of the induction coil. Thus, the distance between successive windings should be larger towards the inlet end of the reactor than towards the outlet end, in order to obtain a higher rate of heating towards the inlet end compared to the heating rate towards the outlet end of the reactor.

Alternative or additionally, the catalyst material may comprise two or more types of catalytic mixtures along the catalyst bed, where the two or more types of catalytic mixtures have different Curie temperatures. If the catalytic mixture closest to the inlet of the reactor unit has a lower Curie temperature than the catalytic mixture closest to the outlet of the reactor, it is possible to control the maximum temperature achievable within the reactor so that it is less close to the inlet end than further along the reactor unit.

Another aspect of the invention relates to a catalytic mixture arranged for catalyzing aromatization of higher hydrocarbons in a reactor in a given temperature range T upon bringing a reactant stream comprising higher hydrocarbons into contact with said catalytic mixture, where the temperature range T is the range from between about 400° C. and about 700° C. or a subrange thereof. The catalytic mixture comprises a catalyst material and a ferromagnetic material, where the catalyst material is arranged to catalyze the aromatization of higher hydrocarbons and the ferromagnetic material is ferromagnetic at least at temperatures up to an upper limit of the given temperature range T.

In an embodiment, the catalytic mixture comprises bodies of catalyst material mixed with bodies of ferromagnetic material.

In an embodiment, the Curie temperature of the ferromagnetic material substantially equals an operating temperature at substantially the upper limit of the given temperature range T of the aromatization reaction.

In an embodiment, the ferromagnetic material is a material comprising iron, an alloy comprising iron and chromium, an alloy comprising iron, chromium and aluminum, an alloy comprising iron and cobalt, or an alloy comprising iron, aluminum, nickel and cobalt.

In an embodiment, the catalyst material comprises a catalytically active material supported on a zeolite. The catalytically active material is e.g. an active phase of one or more of the following elements: zinc, gallium, molybdenum, platinum; and the zeolite is e.g. a HZSM, a ZSM or a SAPO zeolite. Thus, an example of the catalyst mixture is a catalytically active material, e.g. Zn, supported on e.g. HZSM-5.

In an embodiment, the ferromagnetic material of the catalytic mixture comprises one or more ferromagnetic macroscopic supports susceptible for induction heating, where said one or more ferromagnetic macroscopic supports are ferromagnetic at temperatures up to an upper limit of the given temperature range T, where said one or more ferromagnetic macroscopic supports is/are coated with an oxide and where the oxide is impregnated with catalyst material. Non-limiting examples of ferromagnetic macroscopic supports coated with an oxide, which in turn is impregnated with catalyst material, are metallic elements, monoliths or miniliths. The ferromagnetic material may e.g. be cobalt, iron, nickel, an alnico alloy, a FeCr alloy, Permendur or combinations thereof In an embodiment, the catalytic mixture has a predetermined ratio between said catalyst material and said ferromagnetic material.

In an embodiment, the catalytic mixture has a predetermined ratio between the catalyst and the ferromagnetic materials. The predetermined ratio between the catalyst and the ferromagnetic materials may be a predetermined graded ratio varying along a flow direction of the reactor. Hereby, when the catalytic mixture is used in a reactor, it is possible to control the temperature in different zones of the reactor. A radial flow reactor may be used; in this case, the predetermined ratio varies along the radial direction of the reactor.

In an embodiment, catalyst material powder and ferromagnetic material powder are mixed and treated to provide bodies of catalytic mixture, the bodies having a predetermined ratio between catalyst and ferromagnetic materials. In an embodiment, the catalytic mixture comprises bodies of catalyst material mixed with bodies of ferromagnetic material. Such bodies may e.g. be pellets, extrudates or miniliths.

Another aspect of the invention relates to a method for aromatization of higher hydrocarbons in a given temperature range T in a reactor system, where the reactor system comprises a reactor unit arranged to accommodate a catalytic mixture, and where the catalytic mixture comprises a catalyst material and a ferromagnetic material. The catalyst material is arranged to catalyze the aromatization of higher hydrocarbons and the ferromagnetic material is ferromagnetic at least at temperatures up to an upper limit of the given temperature range T, where the temperature range T is the range from between about 400° C. and about 700° C. or a subrange thereof. The reactor system further comprises an induction coil arranged to be powered by a power source supplying alternating current and positioned so as to generate an alternating magnetic field within the reactor unit upon energization by the power source, whereby the catalytic mixture is heated to a temperature within the given temperature range T by means of said alternating magnetic field. The method comprises the steps of:
  (i) Generating an alternating magnetic field within the reactor unit upon energization by a power source supplying alternating current, said alternating magnetic field passing through the reactor unit, thereby heating catalytic mixture by induction of a magnetic flux in the material;
  (ii) bringing a reactant stream comprising higher hydrocarbons into contact with said catalyst material;
  (iii) heating said reactant stream to a temperature within the given temperature range T within said reactor by the generated alternating magnetic field; and
  (iv) letting the reactant stream react in order to provide a product to be outlet from the reactor.

The sequence of the steps (i) to (iv) is not meant to be limiting. Steps (ii) and (iii) may happen simultaneously, or step (iii) may be initiated before step (ii) and/or take place at the same time as step (iv). Advantages as explained in relation to the reactor system and the catalytic mixture also apply to the method for aromatization of higher hydrocarbons. The catalytic mixture may have a predetermined ratio between the catalyst material and the ferromagnetic material.

The Curie temperature of the ferromagnetic material may be equal to or above an upper limit of the given temperature range T of the dehydrogenation reaction. Alternatively, the Curie temperature could be slightly lower than the upper limit of the given temperature range T, in that the reactant gas stream entering the reactor system may be heated to a temperature above the Curie temperature before entering the reactor system, thereby providing an upper limit of the temperature range T—in an upstream part of the reactor unit—which is higher than that obtainable by induction heating.

In an embodiment, the reactant stream is preheated in a heat exchanger prior to step (ii). This improves the overall energy efficiency of the process. As an example only, the reactant stream may be heated to a temperature of between 75° C. and 150° C.

DETAILED DESCRIPTION OF THE FIGURES

Figure 1:
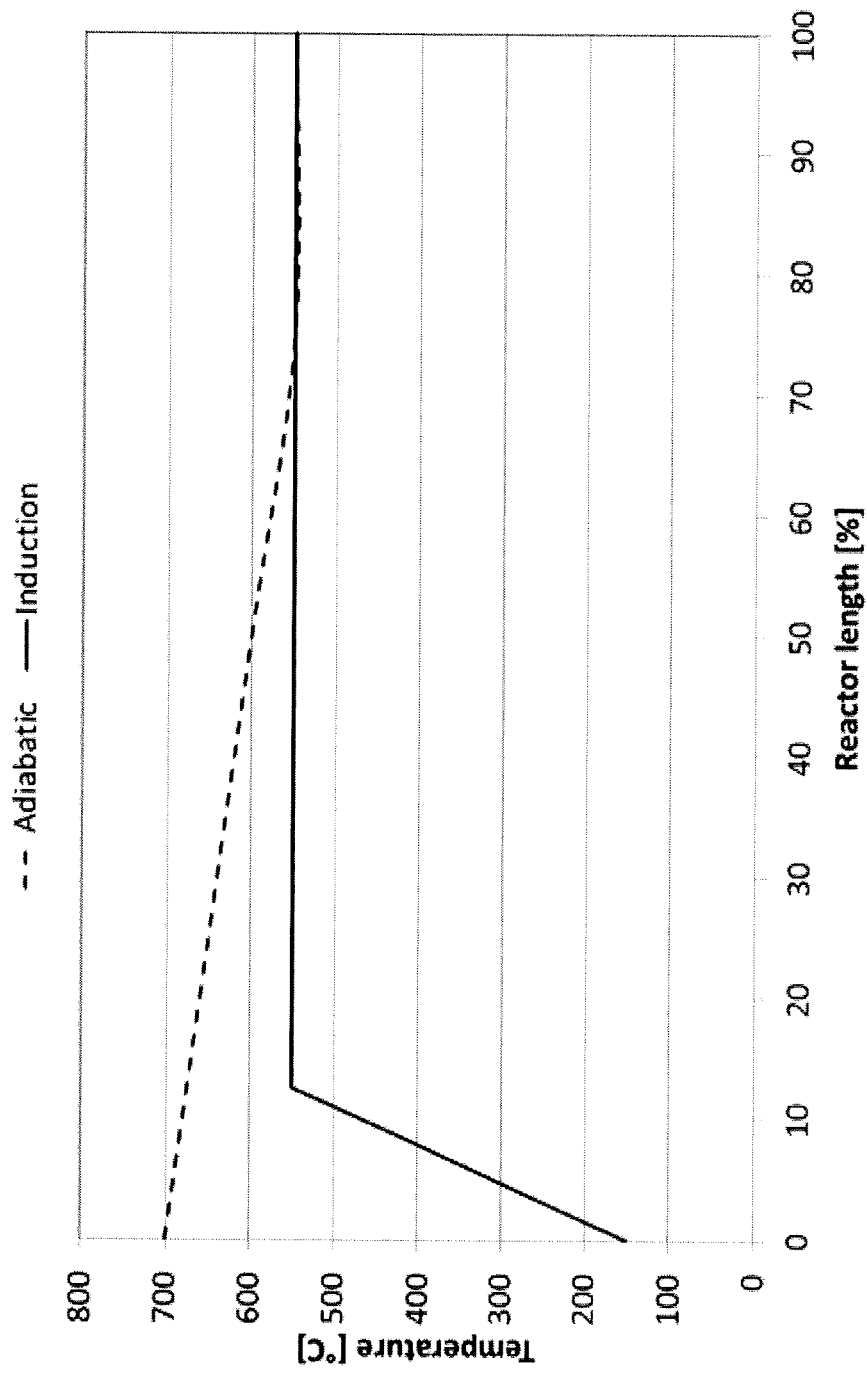
FIG. 1 is a graph showing a temperature profile of catalyst in a reactor unit heated by induction heating as compared to a preheated reactant stream.

FIG. 1 is a graph showing a temperature profile of catalyst in a reactor unit heated by induction heating as compared to a preheated reactant stream.

In both situations, the reactor unit is a longitudinal flow reactor unit comprising catalyst material arranged for carrying out aromatization of higher hydrocarbons, viz. an endothermic reaction. As shown in FIG. 1 this reaction takes place at temperatures between about 550° C. and 700° C.

The dotted line indicates the temperature profile along the length of a reactor for a preheated reactant stream, corresponding to the situation where the reactor is an adiabatic reactor. As shown in FIG. 1, the reactant gas in the situation where the reactor unit is an adiabatic reactor is preheated to a temperature of about 700° C. When the gas passes along the longitudinal direction of the reactor unit, the temperature thereof decreases since the value of the Gibbs free energy of the aromatization reaction is negative. In order to ensure that the temperature of the reactant stream stays above about 550° C. throughout the reactor length, the reactant gas stream has been preheated to about 700° C. even though such a relatively high temperature results in a high risk of carbon formation in the catalyst bed of the reactor.

In comparison, the solid curve shows the temperature throughout the longitudinal direction of the reactor unit in a case where the reactor system and catalyst within the reactor system is arranged for inductive heating. In the situation shown in FIG. 1, the reactant gas stream enters the reactor unit at a temperature of about 150° C. Within the first approximately 10% of the length of the reactor unit, the temperature of the reactant gas stream increases to about 550° C. due to the inductive heating of the catalyst within the reactor unit. The temperature of the gas within the reactor remains at about 550° C. throughout the remaining 90% of the length of the reactor unit.

In addition to the advantageous delivery of heat directly to the catalyst material and the resulting possibility of reducing the maximum temperature of the feed or reactant gas, induction heating offers a fast heating mechanism, which potentially could make upstart of a aromatization reactor relative fast.

Figure 2A:
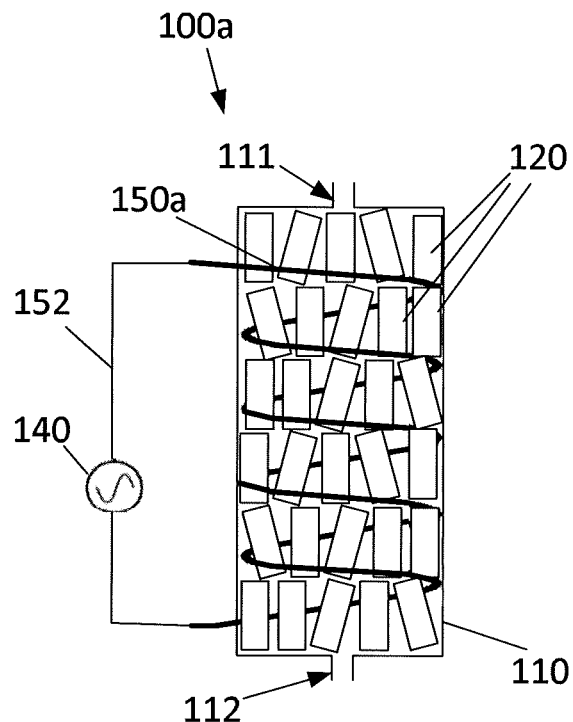
FIGS. 2A and 2B show schematic drawings of two embodiments of a reactor system.
Figure 2B:
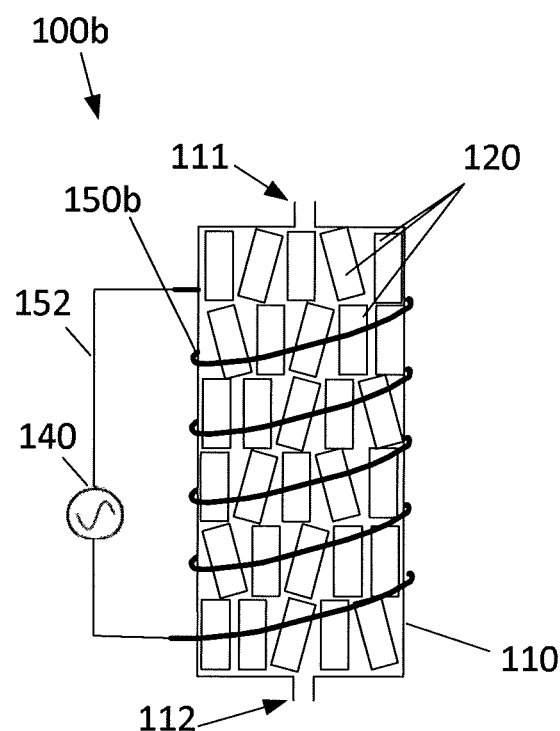

FIGS. 2A and 2B show schematic drawings of two embodiments $100a$ and $100b$, of a reactor system. In FIGS. 2A and 2B, similar features are denoted using similar reference numbers.

FIG. 2A shows an embodiment of the reactor system $100a$ for carrying out dehydrogenation of alkanes to alkenes and subsequent aromatization of the alkenes upon bringing a reactant stream comprising alkanes into contact with a catalytic mixture 120. The reactor system $100a$ comprises a reactor unit 110 arranged to accommodate a catalytic mixture 120 comprising a catalyst material and a ferromagnetic material, where the catalyst material is arranged to catalyze the dehydrogenation of alkanes to alkenes and the subsequent aromatization of alkenes. The ferromagnetic material is ferromagnetic at least at temperatures up to about 600° C.

Reactant is introduced into the reactor unit 110 via an inlet 111, and reaction products formed on the surface of the catalyst mixture 120 is outlet via an outlet 112.

The reactor system $100a$ further comprises an induction coil $150a$ arranged to be powered by a power source 140 supplying alternating current. The induction coil $150a$ is connected to the power source 140 by conductors 152. The induction coil $150a$ is positioned so as to generate an alternating magnetic field within the reactor unit 110 upon energization by the power source 140. Hereby the catalyst mixture 120 is heated to a temperature within a given temperature range T relevant for dehydrogenation of alkanes, such as between 350° C. and about 500° or 700° C., by means of the alternating magnetic field.

The induction coil $150a$ of FIG. 2A is placed substantially adjacent to the inner surface of the reactor unit 110 and in physical contact with the catalytic mixture 120. In this case, in addition to the induction heating provided by the magnetic field, the catalyst material 120 adjacent the induction coil $150a$ is additionally heated directly by ohmic/resistive heating due to the passage of electric current through the windings of the induction coil $150a$. The induction coil $150a$ may be placed either inside or outside the catalyst basket (not shown) supporting the catalytic mixture 120 within the reactor unit 110. The induction coil is preferably made of kanthal.

The catalytic mixture 120 may be divided into sections (not shown in the figures), where the ratio between the catalytic material and the ferromagnetic material is varies from one section to another. At the inlet of the reactor unit 110, the reaction rate is high and the heat demand is large; this may be compensated for by having a relatively large proportion of ferromagnetic material compared to the catalytic material. The ferromagnetic material may also be designed to limit the temperature by choosing a ferromagnetic material with a Curie temperature close to the desired reaction temperature.

Placing the induction coil $150a$ within the reactor unit 110 ensures that the heat produced due to ohmic resistance heating of the induction coil $150a$ remains useful for the dehydrogenation reaction. However, having an oscillating magnetic field within the reactor may cause problems, if the materials of the reactor unit 110 are magnetic with a high coercivity, in that undesirably high temperatures may be the result. This problem can be circumvented by cladding the inside of the reactor unit 110 with materials capable of reflecting the oscillating magnetic field. Such materials could e.g. be good electrical conductors, such as copper. Alternatively, the material of the reactor unit 110 could be chosen as a material with a very low coercivity. Alternatively, the induction coil 150 could be wound as a torus.

To make the catalyst bed susceptible for induction, different approaches may be applied. One approach is to support the catalyst material on the ferromagnetic material. For example, the ferromagnetic material comprises one or more ferromagnetic macroscopic supports susceptible for induction heating, and the one or more ferromagnetic macroscopic supports are ferromagnetic at temperatures up to an upper limit of the given temperature range T. The one or more ferromagnetic macroscopic supports is/are coated with an oxide and the oxide is impregnated with catalyst material. Another approach is to mix catalyst material powder and ferromagnetic material powder and treat the mixture to provide bodies of catalytic mixture. Additionally or alternatively, the catalytic mixture comprises bodies of catalyst material mixed with bodies of ferromagnetic material, wherein the smallest outside dimension of the bodies are in the order of about 1-2 mm or larger.

The catalytic mixture preferably has a predetermined ratio between the catalyst material and the ferromagnetic material. This predetermined ratio may be a graded ratio varying along a flow direction of the reactor.

In another approach, ferromagnetic macroscopic supports are coated with an oxide impregnated with the catalytically active material. This approach offers a large versatility compared to the ferromagnetic nanoparticles in the catalyst, as the choice of catalytic active phase is not required to be ferromagnetic.

FIG. 2B shows another embodiment 100b of the reactor system for carrying out dehydrogenation of alkanes to alkenes and subsequent aromatization of the alkenes upon bringing a reactant stream comprising alkanes into contact with a catalytic mixture 120. The reactor unit 110 and its inlet and outlet 111, 112, the catalytic mixture 120, the power source 140 and its connecting conductors 152 are similar to those of the embodiment shown in FIG. 2A.

In the embodiment of FIG. 2B, an induction coil 150b is wound or positioned around the outside of the reactor unit 110.

In both embodiments shown in FIGS. 2A and 2B, the catalytic mixture can be any catalytic mixture according to the invention. Thus, the catalytic mixture may be in the form of catalyst material supported on the ferromagnetic material, e.g. where in the form of ferromagnetic macroscopic support(s) coated with an oxide, where the oxide is impregnated with catalyst material, miniliths, a monolith, or bodies produced from a mixture of catalyst material powder and ferromagnetic material powder. Thus, the catalyst material is not limited to catalyst material having relative size as compared to the reactor system as shown in the figures. Moreover, when the catalyst material comprises a plurality of macroscopic supports, the catalyst material would typically be packed so as to leave less space between the macroscopic supports than shown in the FIGS. 2A and 2B. Furthermore, in the two embodiments shown in FIGS. 2A and 2B, the reactor unit 110 is made of non-ferromagnetic material. In the two embodiments shown in FIGS. 2A and 2B, the power source 140 is an electronic oscillator arranged to pass a high-frequency alternating current (AC) through the coil surrounding at least part of the catalyst material within the reactor system.

EXAMPLE

The catalyst material comprises for example Zn as the catalytically active material supported on a zeolite, e.g. a HZSM, a ZSM or a SAPO zeolite. The ferromagnetic material is e.g. beads of iron, an alloy comprising iron and chromium, an alloy comprising iron, chromium and aluminum, an alloy comprising iron and cobalt, or an alloy comprising iron, aluminum, nickel and cobalt.

The frequency of the alternating current through the induction coil is e.g. 50 kHz and the alternating current has e.g. a root mean square value of 10 A. Such an alternating current field generates a magnetic field of about 0.05 T. The magnetic field heats the ferromagnetic material, e.g. the FeCrAlloy beads, to a temperature of about 550° C. and the energy is transferred to the catalyst material. When a reactant stream entering the reactor at a temperature of about 100° C., it is rapidly heated to 550° C. which will facilitate aromate synthesis over the catalyst material. The product from the reaction is a mixture of benzene, toluene, xylene, hydrocarbons and hydrogen. In a further step, the product from the reaction may be purified.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. Furthermore, individual features mentioned in different claims may possibly be advantageously combined, and the mentioning of these features in different claims does not exclude that a combination of features is not possible and advantageous.

The invention claimed is:

1. A reactor system for aromatization of higher hydrocarbons within a given temperature range T upon bringing a reactant stream comprising higher hydrocarbons into contact with a catalytic mixture, said reactor system comprising: a reactor unit arranged to accommodate a catalytic mixture, said catalytic mixture comprising a catalyst material and a ferromagnetic material, where said catalyst material is arranged to catalyze the aromatization of higher hydrocarbons and said ferromagnetic material is ferromagnetic at least at temperatures, the curie temperature, up to an upper limit of the given temperature range T, wherein the given temperature range T is the range between about 400° C. and about 700° C., an induction coil arranged to be powered by a power source supplying alternating current and being positioned so as to generate an alternating magnetic field within the reactor unit upon energization by the power source, whereby the ferromagnetic material is heated to a temperature within said temperature range T by means of said alternating magnetic field, wherein said ferromagnetic material comprises one or more ferromagnetic macroscopic supports susceptible for induction heating, where said one or more ferromagnetic macroscopic supports are ferromagnetic at temperatures up to an upper limit of the given temperature range T, where said one or more ferromagnetic macroscopic supports is/are coated with an oxide and where the oxide is impregnated with catalyst material.

2. A reactor system according to claim 1, wherein the Curie temperature of the ferromagnetic material equals an operating temperature at substantially the upper limit of the given temperature range T of the aromatization reaction.

3. A reactor system according to claim 1, wherein the Curie temperature of the ferromagnetic material is above about 500° C.

4. A reactor system according to claim 1, wherein the induction coil is placed within the reactor unit or around the reactor unit.

5. A reactor system for aromatization of higher hydrocarbons within a given temperature range T upon bringing a reactant stream comprising higher hydrocarbons into contact with a catalytic mixture, said reactor system comprising: a reactor unit arranged to accommodate a catalytic mixture, said catalytic mixture comprising a catalyst material and a ferromagnetic material, where said catalyst material is arranged to catalyze the aromatization of higher hydrocarbons and said ferromagnetic material is ferromagnetic at least at temperatures, the curie temperature, up to an upper limit of the given temperature range T, wherein the given temperature range T is the range between about 400° C. and about 700° C., an induction coil arranged to be powered by a power source supplying alternating current and being positioned so as to generate an alternating magnetic field within the reactor unit upon energization by the power source, whereby the ferromagnetic material is heated to a temperature within said temperature range T by means of said alternating magnetic field, wherein said catalytic mixture comprises bodies of catalyst material mixed with bodies of ferromagnetic material, wherein the smallest outer dimension of a plurality of the bodies are in the order of about 1-2 mm or larger.

6. A reactor system according to claim 5, wherein the catalytic mixture has a predetermined ratio between said bodies of catalyst material and said bodies of ferromagnetic material.

7. A reactor system according to claim 5, wherein the predetermined ratio between said catalyst and said ferromagnetic materials is a predetermined graded ratio varying along a flow direction of said reactor.

8. A reactor system according to claim 5, wherein the Curie temperature of the ferromagnetic material equals an operating temperature at substantially the upper limit of the given temperature range T of the aromatization reaction.

9. A reactor system according to claim 5, wherein the Curie temperature of the ferromagnetic material is above about 5000 C.

10. A reactor system according to claim 5, wherein the induction coil is placed within the reactor unit or around the reactor unit.

11. A reactor system for aromatization of higher hydrocarbons within a given temperature range T upon bringing a reactant stream comprising higher hydrocarbons into contact with a catalytic mixture, said reactor system comprising: a reactor unit arranged to accommodate a catalytic mixture, said catalytic mixture comprising a catalyst material and a ferromagnetic material, where said catalyst material is arranged to catalyze the aromatization of higher hydrocarbons and said ferromagnetic material is ferromagnetic at least at temperatures, the curie temperature, up to an upper limit of the given temperature range T, wherein the given temperature range T is the range between about 400° C. and about 700° C., an induction coil arranged to be powered by a power source supplying alternating current and being positioned so as to generate an alternating magnetic field within the reactor unit upon energization by the power source, whereby the ferromagnetic material is heated to a temperature within said temperature range T by means of said alternating magnetic field, wherein the distance between windings of said induction coil varies along the flow direction of the reactor.

12. A reactor system according to claim 11, wherein the Curie temperature of the ferromagnetic material equals an operating temperature at substantially the upper limit of the given temperature range T of the aromatization reaction.

13. A reactor system according to claim 11, wherein the Curie temperature of the ferromagnetic material is above about 500° C.

14. A reactor system according to claim 11, wherein the induction coil is placed within the reactor unit or around the reactor unit.

\* \* \* \* \*